US007923586B2

(12) United States Patent
Stahlbush et al.

(10) Patent No.: US 7,923,586 B2
(45) Date of Patent: Apr. 12, 2011

(54) METHOD FOR STABILIZING A CATION EXCHANGE RESIN PRIOR TO USE AS AN ACID CATALYST AND USE OF SAID STABILIZED CATION EXCHANGE RESIN IN A CHEMICAL PROCESS

(75) Inventors: James Richard Stahlbush, Midland, MI (US); Katherine H. Stahlbush, legal representative, Midland, MI (US); Harlan Robert Goltz, Midland, MI (US); Thomas Caldwell Young, Lake Jackson, TX (US); Edward Alan Fraini, Spring, TX (US)

(73) Assignee: Dow Global Technologies LLC

( * ) Notice: Subject to any disclaimer, the term of this patent is extended or adjusted under 35 U.S.C. 154(b) by 184 days.

(21) Appl. No.: 11/792,935

(22) PCT Filed: Jan. 24, 2006

(86) PCT No.: PCT/US2006/002279
§ 371 (c)(1),
(2), (4) Date: Apr. 10, 2008

(87) PCT Pub. No.: WO2006/083602
PCT Pub. Date: Aug. 10, 2006

(65) Prior Publication Data
US 2008/0319237 A1      Dec. 25, 2008

Related U.S. Application Data

(60) Provisional application No. 60/647,866, filed on Jan. 28, 2005.

(51) Int. Cl.
*C07C 37/20* (2006.01)

(52) U.S. Cl. ...................................................... 568/728
(58) Field of Classification Search ....................... None
See application file for complete search history.

(56) References Cited

U.S. PATENT DOCUMENTS

| | | | | |
|---|---|---|---|---|
| 3,394,089 | A * | 7/1968 | McNutt et al. | 521/33 |
| 4,584,416 | A * | 4/1986 | Pressman et al. | 568/727 |
| 4,820,740 | A * | 4/1989 | Li | 521/32 |
| 4,973,607 | A * | 11/1990 | Stahlbush et al. | 521/28 |
| 5,075,511 | A * | 12/1991 | Li | 568/727 |
| 5,302,623 | A * | 4/1994 | Dhingra et al. | 521/38 |
| 6,472,479 | B1 * | 10/2002 | Kohler et al. | 525/344 |
| 6,723,881 | B1 * | 4/2004 | Bodiger et al. | 568/335 |

OTHER PUBLICATIONS

Database CAPLUS on STN, Acc. No. 2001:152320, Kohler et al., EP 1078940 (Feb. 28, 2001) (abstract).*
Database CAPLUS on STN, Acc. No. 1998:352761, Wakita et al., WO 9822217 (May 28, 1998) (abstract).*
Database CAPLUS on STN, Acc. No. 1994:193234, Chalabiev et al., SU 1728250 (Apr. 23, 1992).*
Database CAPLUS on STN, Acc. No. 1981:462945, Juracka et al., CS 184988 (Sep. 15, 1978) (abstract).*

* cited by examiner

*Primary Examiner* — Brian J Davis

(57) ABSTRACT

A method for preventing the degradation of a catalyst during storage of the catalyst and prior to using the catalyst in a chemical process comprising treating the catalyst with an antioxidant and storing the treated catalyst until further use. The stabilized treated catalyst may be used in a process for producing organic chemicals such as in a process for producing bisphenol A.

16 Claims, No Drawings

METHOD FOR STABILIZING A CATION EXCHANGE RESIN PRIOR TO USE AS AN ACID CATALYST AND USE OF SAID STABILIZED CATION EXCHANGE RESIN IN A CHEMICAL PROCESS

CROSS REFERENCE TO RELATED APPLICATION

This application is a 371 of PCT/US2006/002279 filed Jan. 24, 2006, which claims the benefit of U.S. Provisional Application Ser. No. 60/647,866 filed Jan. 28, 2005.

The present invention relates to stabilizing a strong acid ion exchange resin for use as an acid catalyst to protect the resin from oxidative degradation and the use of said stabilized ion exchange resin in chemical production processes. More particularly, the present invention relates to the treatment of a strong acid ion exchange resin for use as an acid catalyst with an antioxidant to protect the resin from oxidative degradation and the use of said treated ion exchange resin in chemical production processes.

Polymeric ion exchange resins, such as styrene-divinylbenzene types of strong acid ion exchange resins are used as catalysts in the production of various organic chemicals including for example bisphenol-A and phenol alkylation. These catalysts are susceptible to oxidation during manufacture, storage, handling, processing, washing, and drying prior to use. Oxidative degradation leads to the release of low and medium molecular weight acidic material from the polymeric resins, such as low molecular weight organic sulfonates, sulfonated oligomers and sulfonated polystyrene polymers. Release of these acidic components into, for example, a bisphenol production process can lead to the generation of undesired impurities and color bodies, resulting in the production of off-spec product.

There is a need to protect ion exchange resins from oxidative degradation prior to and during storage; prior to and during washing; prior to and during drying; and prior to use of the ion exchange resin in a chemical production process.

U.S. Pat. No. 4,973,607 discloses a method of stabilizing a cation exchange resin against oxidation by treating the resin with an antioxidant and then using the stabilized antioxidant-treated cation exchange resin exclusively for water applications, wherein the purpose of the stabilization is to prevent decomposition of resin during such use of the stabilized resin.

U.S. Pat. No. 4,973,607 does not disclose the use of an antioxidant-stabilized ion exchange resin in catalytic chemical processes such as bisphenol-A or phenol alkylation production; and does not disclose that the purpose of stabilization is to prevent degradation of the cation exchange resin prior to use as a catalyst. Oxidative decomposition of cation exchange resins during use as catalysts in chemical processes is generally not an issue in the industry, because oxygen is typically excluded from chemical production processes due to flammability concerns. Also, in many chemical production processes, such as the manufacture of bisphenol-A, the catalyst is immersed in a process stream which is typically also a very good antioxidant. Therefore, there is still a need in the industry for stabilizing a catalyst prior to use in a chemical process.

U.S. Pat. No. 4,973,607 also does not recognize that antioxidant stabilization makes ion-exchange resins easier to wash prior to use as a catalyst. In addition, U.S. Pat. No. 4,973,607 does not recognize that leachable material may be acidic in nature, and that the release of this acidic material, for example in a bisphenol-A production process or in other processes in which an ion-exchange resin is used as a catalyst, could cause significant production problems. For example, Stahlbush et al., "Prediction and Identification of Leachables from Cation Exchange Resins", Proceedings of 48th International Water Conference, Nov. 2-4, 1987; and Stahlbush et al., "Identification, Prediction and Consequence of the Decomposition Products from Cation Exchange Resins", in "IEX'88-Ion Exchange for Industry", M. Streat, editor, Ellis Horwood, Chichester, 1988; describes leachables produced by the oxidation of cation exchange resins, describes a test for accelerated aging of the resins, describes the levels of leachables produced by different types of resins, and shows that anion exchange resins are not effective in adsorbing sulfonated polystyrene leachables of higher molecular weight.

Japanese Patent Publication 20021132(A), Japanese Patent Publication 20021133(A) and Japanese Patent Publication 20021134(A) specifically address degradation of the thiol portion of an aminothiol promoter of a bisphenol-A ion exchange resin catalyst which has been modified with an aminothiol promoter, but do not teach preventing degradation of the ion-exchange catalyst itself.

Ion exchange resin catalysts are normally washed prior to use to remove contaminants that can affect the operation of the process. Methods of optimizing the washing of the catalyst prior to use have been previously disclosed, for example, in European Patent 765685; U.S. Pat. No. 6,723,881; U.S. Pat. No. 5,723,691; Japanese Patent Publication 2000143565 (A); and Japanese Patent Publication Kokai 09010598(A). U.S. Pat. No. 6,723,881 discloses, as part of a catalyst preparation procedure, the use of "water free of dissolved oxygen" in the water washing step. The catalyst preparation procedure is taught as being effective in removing oligomer content which occurs as a part of the catalyst production process; catalyst degradation is not discussed in U.S. Pat. No. 6,723,881.

The prior known technologies described above relate to methods of removing leachable material from a catalyst prior to its use. What is needed in the industry is a method that will prevent the leachable material from being formed in the first place, that is, from being formed prior to use of the ion-exchange resin as a catalyst. The prior known technologies described above relate to methods which are used to remove leachable material after the leachable material has been formed.

It is, therefore, desired to provide an economical method for stabilizing an ion-exchange resin to prevent degradation of the resin prior to its use as a catalyst.

One aspect of the present invention is directed to stabilizing a strong acid ion exchange resin for use as an acid catalyst to protect the resin from oxidative degradation and the use of said stabilized ion exchange resin in chemical production processes.

The degradation of ion exchange resin catalysts during storage and prior to use may be prevented by storing the resin in the absence of oxygen, for example, by using oxygen barrier packaging, inert gas blanketing or vacuum packaging or some other method that excludes oxygen from contacting the catalyst.

Another aspect of the present invention is directed to a method for preventing the degradation of a catalyst during storage of the catalyst which may be subjected to contact with an oxygen environment and prior to using the catalyst in a chemical process comprising treating the catalyst with an antioxidant. In this instance, the antioxidant-treated catalyst can then be stored without taking special precautions to prevent contact with oxygen until further use.

Still another aspect of the present invention is directed to a process for producing a chemical product in a chemical process using a catalyst comprising (a) treating the catalyst with an antioxidant; and (b) contacting the catalyst with the necessary reactants to produce the chemical product in such chemical process.

One embodiment of the chemical process for producing a chemical product using a treated catalyst of the present invention is, for example, a process for producing bisphenol A.

One objective of the present invention is to stabilize a strong acid ion exchange resin for use as an acid catalyst to protect the resin from oxidative degradation and the use of said stabilized ion exchange resin in chemical production processes, for example in the production of bisphenol A.

For the purposes of describing the present invention, the "stability" of the resin refers to the resin's ability to withstand decomposition during storage, handling, processing, and drying. Decomposition is primarily caused by oxidation and can result in unwanted color throw, leachables and elevated total organic carbon (TOC) levels which can in turn affect the resins performance and perceived quality. A stabilized resin resists oxidation upon storage, handling, processing, and drying. Improving the stability of the resin enhances the resins ability to resist oxidative decomposition after long periods of storage, handling, processing, and drying eliminating the color throw, leachables and elevated TOC levels when such resin is brought into service.

Oxidative degradation can be observed as a progressive discoloration of a cation exchange resin sample when stored without special precautions to prevent oxygen contact. Immersion of such a sample in water would result in a discoloration of the water, and a noticeable increase in the acidity and the TOC content of the water. An ion exchange resin that resists oxidative degradation is said to have good shelf life, and would not discolor significantly on storage, nor cause a large increase in water color, acidity or TOC content when placed in water. Typical unstabilized cation exchange resins do not have good shelf life, and begin to discolor after storage of one month or less. A stabilized catalyst of the present invention, on the other hand, will have a shelf life of generally three months or more, preferably six months or more, and most preferably greater than one year.

One embodiment of the present invention for preventing the degradation of the ion exchange resin is to store the resin in such a way as to prevent exposure of the resin to oxygen, that is, in a way that prevents the resin from coming into contact with oxygen before further use. Various means of preventing contact with oxygen may be used, including the use of oxygen barrier packaging, inert gas blanketing or vacuum packaging or some other method that excludes oxygen from contacting the catalyst. Cation exchange resins are often packaged in a water wet condition, and the packaging used is typically a good barrier for water transmission but not for oxygen transmission. For the purposes of the present invention, the preferred oxygen barrier packaging would have an oxygen permeability of 250 cc/m$^2$.atm.day or less. Packaging with an oxygen permeability of 100 cc/m$^2$.atm.day or less is preferred, and an oxygen permeance of 50 cc/m$^2$.atm.day or less is most preferred.

Preferred inert gases for blanketing include gases which have low oxygen content and are generally considered to be unreactive. More preferred gases include, for example, nitrogen, argon, carbon dioxide and mixtures thereof. Nitrogen is the most preferred gas. The oxygen content of the gas used for blanketing is preferable less than 5 percent and more preferably less than 1 percent. The inert gas blanketing would preferably be used in combination with the oxygen barrier packaging described above.

If vacuum packaging is used, the package is evacuated to remove air. Preferably, the package is evacuated so that the gas pressure in the package is less than 0.25 atmosphere (atm). More preferably, the gas pressure in the package is less than 0.1 atm. If the cation exchange resin is packaged in a water wet condition, the gas pressure in the vacuum package is preferably no more than 0.1 atm over the vapor pressure of water at the temperature of the package.

One preferred embodiment of the present invention for preventing the degradation of the ion exchange resin includes treating the ion exchange resin with an antioxidant. The antioxidant and the steps necessary to apply the antioxidant to the ion exchange resin are described below. The antioxidant is added to the ion exchange resin, preferably at the time of manufacture of the ion-exchange resin, to prevent degradation of the resin by suppressing the free-radical mechanism.

The ion exchange resin used in the present invention includes, for example, a cation exchange resin. Cation exchange resins and processes for preparing cation exchange resins are well known in the art, as exemplified in Helfferich, *Ion Exchange*, McGraw-Hill Book Co., Inc., pp. 26-47 (1962). Advantageously, the resins are prepared by first copolymerizing one or more monovinyl monomers and one or more polyvinyl monomers to prepare a crosslinked copolymer matrix, and then functionalizing the copolymer matrix with groups which can exchange cations. Preferred monovinyl monomers include styrene and its derivatives, acrylic or methacrylic acid, esters of acrylic or methacrylic acid and mixtures thereof. More preferred monovinyl monomers are the monovinyl aromatic monomers, styrene being the most preferred. Preferred polyvinyl monomers include divinylbenzene (DVB) (commercially available DVB containing less than 45 weight percent ethylvinylbenzene), trivinylbenzene, and diacrylates or dimethacrylates. More preferred polyvinyl monomers are divinyl monomers, especially divinyl aromatic monomers. The most preferred polyvinyl monomer is DVB. A small amount of a third monomer may be added. Such monomers include for example polyacrylonitrile and ethylene glycol dimethacrylate. Amounts of such monomer may be, for example, less than 10 wt percent, preferably less than 5 wt percent, and more preferably less than 3 wt percent. The copolymer matrix is advantageously functionalized with sulfonic, phosphinic, phosphonic, arsenic, or carboxylic acid groups, or phenolic groups. The copolymer matrix is preferably functionalized with sulfonic acid groups.

Cation exchange resins useful in the present invention include for example styrene-divinylbenzene types of strong acid ion exchange resins such as DOWEX 50WX4, DOWEX 50WX2, DOWEX M-31, DOWEX MONOSPHERE M-31, DOWEX DR-2030 and DOWEX MONOSPHERE DR-2030 catalysts commercially available from The Dow Chemical Company.

Other examples of commercially available ion exchange resins useful in the present invention include Diaion SK104, Diaion SK1B, Diaion PK208, Diaion PK212 and Diaion PK216 manufactured by Mitsubishi Chemical Industries, Limited; A-15, A-35, A-121, A-232 and A-131 manufactured by Rohm & Haas; T-38, T-66 and T-3825 manufactured by Thermax; Lewatit K1131, Lewatit K1221, Lewatit K1261 and Lewatit SC 104 manufactured by Bayer; Indion 180 and Indion 225 manufactured by Ion Exchange India Limited; and Purolite CT-175, Purolite CT-222 and Purolite CT-122 manufactured by Purolite.

The sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. The sulfonated styrene-divinyl benzene copolymer copolymer being preferred. These resins can be used in gel, porous, or seeded (U.S. Pat. No. 4,564,644; U.S. Pat. No. 5,834,524; U.S. Pat. No. 5,616,622; U.S. Pat. No. 4,419,245) forms. These resins can have narrow (U.S. Pat. No. 4,427,794; U.S. Pat. No. 4,444,961; U.S. Pat. No. 3,922,255) or broad particle size distributions. These resins can also be sulfone cross-linked (EP1222960A2), shell functionalized (EP0552541A1, U.S. Pat. No. 5,081,160) and or contain greater than 1 sulfonic acid group per benzene ring. And these resins can be used singly or in combinations of two or more.

Antioxidants that may be used in the present invention include soluble antioxidants, bound antioxidants and antioxidants incorporated into the backbone of the cation exchange resin polymer. Soluble antioxidants can be applied to the ion exchange resin by dissolving them in water, then mixing the water dissolved antioxidant with the cation resin. When the excess liquid is drained from the resin, a portion of the antioxidant would be retained in the water absorbed by the cation resin, if the cation resin is left in a "water wet" condition. In some cases, if desired, the soluble antioxidants can be removed from the cation resin prior to use; and in such cases the antioxidant may be removed from the cation resin prior to use by washing.

Bound antioxidants contain functionalities that cause the antioxidants to become bound to the sulfonic acid groups of the cation resin. For example, 2,6-di-t-butyl-α-dimethylamino-p-cresol contains an amine group, a weak base, which binds strongly to the sulfonic acid groups of the cation resin, and can only be rinsed off by using strong acids or by neutralizing the strong acid groups (neutralization would render the cation resin unusable as a strong acid catalyst).

Antioxidants incorporated into the backbone of the cation exchange resin polymer by copolymerization include monomers with antioxidant properties that can be reacted with the other monovinyl and/or polyvinyl monomers to be made part of the resin polymer structure. Monomers with antioxidant activity may be incorporated into the polymer backbone of the ion-exchange resin during copolymer preparation prior to sulfonation. For example, EP 1078941 describes an ion-exchange resin containing a vinylpyridine as a comonomer, wherein the vinylpyridine, which is incorporated into the polymer, acts as an antioxidant. EP 1078940 describes ion-exchange resins containing phenol derivatives as a comonomer, in which the phenol derivative incorporated into the polymer acts as an antioxidant.

The antioxidant useful in the present invention are substances which retard deterioration of the cation exchange resin by oxidation over time and may include for example those described in U.S. Pat. No. 4,973,607. In addition the antioxidants used in the present invention may include those described in Dexter et al., *Encyclopedia of Polymer Science and Technology*, Copyright© 2002 by John Wiley & Sons, Inc.; Thomas et al., *Kirk-Othmer Encyclopedia of Chemical Technology*, Copyright©2002 by John Wiley & Sons; Ash, Michael and Irene, *The Index of Antioxidants and Antiozonants*, Copyright 1997 by Gower; Denisov, E. T., *Handbook of Antioxidants*, Copyright 1995 by CRC Press; and *Index of Commercial Antioxidants and Antiozonants*, Copyright 1983 by Goodyear Chemicals; all of which are incorporated here by reference.

Antioxidants which may be used in the present invention, include for example, monocyclic of polyclyclic phenols, amines, diamines, hydroxylamines, thioesters, phosphites, quinolines, benzofuranones, or mixtures thereof. The antioxidant should preferably be unreactive in the chemical process for which the cation resin is intended, especially if a bound or copolymerized type of antioxidant is used. Other possible types of antioxidants that may be used in the present invention are described in U.S. Pat. No. 4,973,607.

Other examples of antioxidants useful in the practice of the present invention may include various chemical preservatives that are substances generally recognized as safe (GRAS) based upon the Code of Federal Regulations, for Food and Drugs, 21CFR182.1 Subpart D-Chemical Preservatives, reference 21CFR Parts 170-199, Apr. 1, 2001 revision. The preferred chemical preservatives for cation exchange resin are used to improve storage and to control color throw and TOC for long term storage. The additive to a typical strong acid cation exchange resin stabilizes said resin to reduce both visual and extractive color throw and to retard the development of TOC leachables. The antioxidants or preservatives are either GRAS or have been tested and approved for using in indirect food contacting applications. Examples of GRAS chemical preservatives can be found in Table I as listed in the Code of Federal Regulations 21, Part 182.1 Subpart D or as commercially tested and approved for indirect food contacting.

TABLE I

Antioxidants/Chemical Preservatives Known to GRAS as Listed in 21CFR182.1 Subpart D

| | |
|---|---|
| 182.3013 | Ascorbic acid |
| 182.3041 | Erythorbic acid |
| 182.3089 | Sorbic acid |
| 182.3109 | Thiodipropionic acid |
| 182.3149 | Ascorbyl palmitate |
| 182.3225 | Calcium sorbate |
| 182.3280 | Dilauryl thiodipropionate |
| 182.3637 | Potassium metabisulfite |
| 182.3640 | Potassium sorbate |
| 182.3731 | Sodium ascorbate |
| 182.3739 | Sodium bisulfite |
| 182.3766 | Sodium metabisulfite |
| 182.3795 | Sodium sorbate |
| 182.3798 | Sodium sulfite |
| 182.3862 | Sulfur dioxide |
| 182.3890 | Tocopherols |

Preferred examples of preservatives used in the present invention include erythorbic acid, thiodipropionic acid, potassium metabisulfite, ascorbic acid and Ethanox 703, ascorbyl palmitate, sorbic acid, vitamin E, 1,3,5,-trimethyl-2,4,6-tris(3,5-di-tert-butyl-4-hydroxybenzyl)benzene (Ethanox 330), and octadecyl-3-(3,5-di-T-butyl-4-hydroxphenyl) propionate (Ethanox 376).

A preferred antioxidant used in the present invention is 2,6-di-t-butyl-α-dimethylamino-p-cresol, an antioxidant sold under the tradename Ethanox 703 by Albemarle Corporation.

The cation resin should preferably contain enough antioxidant to effectively prevent oxidation of the resin prior to use. If a bound antioxidant is used, the cation resin should not contain so much antioxidant that the functionality of the acid resin is impaired. A permissible range might include an antioxidant content of from 0.001 to 10 percent of the cation resin by weight. A preferable range of antioxidant content may be from 0.01 to 0.5 percent by weight.

Various methods may be used to apply the antioxidant to the cation resin. For example, in one embodiment, the antioxidant may be applied to the cation resin by first preparing a solution of the antioxidant in water, and then mixing the aqueous antioxidant solution with the cation resin until at least a portion of the antioxidant present in the solution is adsorbed by the cation resin. The excess solution is then drained from the cation resin.

The aqueous antioxidant solution may contain other components that are either optional or necessary to form the solution. For example, the antioxidant 2,6-di-t-butyl-α-dimethylamino-p-cresol is sparingly soluble in water, and therefore an acid such as hydrochloric acid is preferably used to form an amine salt so that the antioxidant will become soluble.

Optionally, the cation resin may be rinsed after the antioxidant solution is applied to remove the unabsorbed elements of the antioxidant from the resin. This rinsing step is particularly desirable if a bound antioxidant, such as 2,6-di-t-butyl-α-dimethylamino-p-cresol, is used; or if the antioxidant solution also contains other components that might cause problems in the subsequent use of the cation resin. For example, when treating a cation resin with a solution containing the hydrochloric acid salt of 2,6-di-t-butyl-α-dimethylamino-p-cresol, hydrochloric acid may be released. Thus, it may be preferable to rinse the hydrochloric acid from the stabilized cation resin after applying the hydrochloric acid salt of 2,6-di-t-butyl-α-dimethylamino-p-cresol to the cation resin.

Optionally, the antioxidant application step can be combined with an existing step in the manufacturing process of the cation resin. For example, one step in a cation resin manufacturing process is the sulfonation of the cation resin using sulfuric acid; and after the sulfonation step of the cation resin, sulfuric acid is present and must be rinsed from the resin. Application of the sulfuric acid salt of 2,6-di-t-butyl-α-dimethylamino-p-cresol could be done before the rinsing step is complete; since the application would release sulfuric acid, the rinsing of this sulfuric acid and the final traces of the residual sulfuric acid from the resin during manufacturing of the resin could be done at the same time.

The stabilized cation resin of the present invention may be used in various chemical production processes where a catalyst is used and wherein there is a need to prevent catalyst oxidation regardless of the final end use. Such processes can include, for example, condensation reactions of phenols and ketones; phenol/acetone production; phenol or cresol alkylation; production of methyl-t-butyl ether (MTBE) or other ethers by addition of an alcohol to an alkene; acrylic or aliphatic ester production by esterification or transesterification; isopropanol manufacture; butene oligomerization; phenylphenol production; interconverting MTBE with t-amyl-methyl ether (TAME), methyl isobutyl ketone (MIBK) production; dianone production that is reduced to o-Phenyl phenol; acrylic- and methacrylic ester production for fibers; and dihydric phenol 2,2bis(4'-hydroxyphenyl) propane production. The antioxidants of the present invention are useful in processes wherein color and acid throw may be a problem and offer the potential to make cleaner, lower color solvents and the reduction of acid release.

The stabilized cation resin is preferably used in a process for producing the dihydric phenol 2,2bis(4'-hydroxyphenyl) propane (commonly referred to as "bisphenol A") which is commercially prepared by condensing 2 moles of phenol with a mole of acetone in the presence of an acid catalyst. A mole of water co-product is coproduced. The bisphenol A process is a well-known process and is described, for example in U.S. Pat. Nos. 4,400,555; 6,703,530; 6,307,111; 6,465,697; and 6,737,551.

The strong acid cation resins of the present invention generally show both a low color throw and a low TOC leachables after treatment with the antioxidant described above. Such benefits are shown after the resin is stored, for example, for up to 6 months with no significant increase in color throw and TOC leachables.

Colorimetric testing methods can be applied to evaluate for color throw. Such testing as well as visual observation is often applied at the point of packaging a resin to assure the quality as manufactured is acceptable and that the resin has been properly processed and washed. Resins may develop color upon storage, which are both measurable by a colorimetric test and/or visual observation. Color throw may impart undesirable colored materials into a process stream.

One method for testing the oxidative stability of cation exchange resins is to use an accelerated aging test. An example of such a test is described as follows: 100 mL of water wet cation exchange resin and 500 mL of deionized water are placed in a jacketed flask and stirred to equilibrate the mixture. Initial samples of the water are removed for analysis. The flask contents are heated to 80° C. Pure oxygen is bubbled through the flask at approximately 50 cubic centimeters/minute, while the contents are agitated by stirring. A condenser is used to prevent the evaporative loss of water from the flask. The flask contents are maintained in contact with oxygen at 80° C. for 7 days. At the end of 7 days, the samples of water are removed for analysis. The above procedure shall be hereafter referred to as the Accelerated Aging Test.

In the present invention, the increase in the color of the water after 7 days in the above test should be no more than 500 APHA as measured by a Hunterlab Color Quest analyzer or other known color analyzers. The amount of color throw may also depend upon the application use and the acceptable levels in such application.

Organic extractives for cation ion exchange resins can be measured using a number of known TOC testing methods such as for example a Shimadzu TOC analyzer. In the present invention, the increase in the TOC levels of the water after seven days in the above test should be no more than 500 ppm as measured by a Shimadzu TOC analyzer or equivalent instrument. The amount of TOC will also depend upon the application use and the acceptable levels in such application.

The following examples are included herein to illustrate the present invention; and are not to limit the scope of the present invention.

EXAMPLE 1

Part A: Application of the Antioxidant

In this Part A of Example 1, varying amounts of an antioxidant, 2,6-di-t-butyl-α-dimethylamino-p-cresol, were incorporated into a styrene/divinylbenzene gel cation exchange resin sold commercially by The Dow Chemical Company under the trademark DOWEX 50WX4.

In a first step, solutions of the antioxidant and an acid in water were prepared by adding the desired amount of the antioxidant and the acid to deionized water and then stirring the mixture until the materials dissolved in the water.

In a second step, 100 mL of the antioxidant solution and 100 mL (80 g) of a well-washed water-wet cation resin were combined in a flask and stirred for 30 minutes. After 30 minutes, the antioxidant solution and the cation resin were separated by filtration and the cation resin was washed thoroughly with deionized water to remove any traces of acid from the resin.

Uptake of the antioxidant on the resin was estimated by analyzing the solution's level of total organic carbon (TOC) before and after the cation resin was treated. The use of TOC for uptake estimation is approximate; since the TOC measurement may respond to components that leach from the resin, the actual uptake may be greater than the calculated estimate. The treatment solution composition (antioxidant solution) and the uptake data are listed in Table 1. Uptake of this bound antioxidant is accomplished by partial neutralization of the acid groups on the cation resin with the amine group of the antioxidant. The fraction of the acid groups neutralized was calculated and is also listed in Table 1. Nine catalyst samples were prepared in this Part A of Example 1: Samples 1-8 were treated with antioxidant and Sample 9(C) is a comparative sample containing no antioxidant.

TABLE 1

Application of the Antioxidant

| | SAMPLE NUMBER | | | | | | | | |
|---|---|---|---|---|---|---|---|---|---|
| | 1 | 2 | 3 | 4 | 5 | 6 | 7 | 8 | 9(C) |
| SOLUTION PREPARATION | | | | | | | | | |
| Acid Type | HCl | HCl | HCl | HCl | $H_2SO_4$ | $H_2SO_4$ | $H_3PO_4$ | $H_3PO_4$ | None |
| Acid Concentration (N) | 1 | 1 | 1 | 1 | 1 | 1 | 1 | 1 | |
| Acid Amount (mL) | 7 | 2.1 | 0.7 | 50 | 27 | 100 | 38 | 150 | |
| Antioxidant Amount (g) | 1 | 0.3 | 0.1 | 1 | 1 | 1 | 1 | 1 | None |
| Total Solution Amount (g) | 1000 | 1000 | 1000 | 1000 | 1000 | 1000 | 1000 | 1000 | |
| Acid Concentration in solution (N) | 0.007 | 0.0021 | 0.0007 | 0.05 | 0.027 | 0.1 | 0.038 | 0.15 | |
| Antioxidant Concentration in solution (percent) | 0.1 | 0.03 | 0.01 | 0.1 | 0.1 | 0.1 | 0.1 | 0.1 | |
| ANTIOXIDANT APPLICATION | | | | | | | | | |
| Cation Resin Amount (mL) | 100 | 100 | 100 | 100 | 100 | 100 | 100 | 100 | 100 |
| Solution Amount (mL) | 100 | 100 | 100 | 100 | 100 | 100 | 100 | 100 | 0 |
| Initial TOC (ppm) | 764 | 236 | 77 | 798 | 836 | 824 | 804 | 819 | N/A |
| Final TOC (ppm) | 31 | 93 | 3 | 5 | 3.4 | 6 | 3.4 | 51 | N/A |
| Antioxidant Uptake (percent) | ≧96 | ≧60 | ≧96 | ≧99.4 | ≧99.6 | ≧99.3 | ≧99.6 | ≧94 | N/A |
| Antioxidant Concentration on Resin (percent by weight) | 0.12 | 0.023 | 0.012 | 0.12 | 0.12 | 0.12 | 0.12 | 0.12 | 0 |
| Resin Acid Content Neutralized (percent) | 0.28 | 0.053 | 0.028 | 0.28 | 0.28 | 0.28 | 0.28 | 0.28 | 0 |

As shown in Table 1 above, greater than 90 percent of the antioxidant was taken up by the cation resin in all of the samples but one (Sample 2). The results in Table 1 show that the uptake of the antioxidant is not strongly affected by the type and amount of acid used. This is demonstrated even though in some cases a significant excess of acid was used over the amount necessary to form a salt of the antioxidant.

Part B: Catalyst Aging

In this Part B of Example 1, an Accelerated Aging Test was carried out on the catalyst to show that an antioxidant suppresses degradation of a cation resin. The testing is designed to simulate the aging of the catalyst.

100 mL of a catalyst sample and 500 mL of deionized water were placed in a jacketed flask. Then the flask contents were heated to 80° C. Pure oxygen was bubbled through the flask contents at approximately 50 cubic centimeters/minute, while the contents were agitated by stirring. A condenser was used to prevent the evaporative loss of water from the flask. The flask contents were maintained in contact with oxygen at 80° C. for up to 7 days, and samples of the water were removed periodically for pH, TOC and color analysis.

Color analysis was done using a HunterLab Color Quest calorimeter. TOC analysis was done using a Shimadzu analyzer. Samples 1, 2, 3 and 9(C) from Part A of Example 1 were tested in this way, and the results are shown in Table 2.

TABLE 2

Results of Accelerated Aging Test
Effect of Antioxidant Concentration on Oxidation

| | SAMPLE NUMBER | | | | | | | | | | | |
|---|---|---|---|---|---|---|---|---|---|---|---|---|
| | 9 (C) | | | 1 | | | 2 | | | 3 | | |
| | Antioxidant Concentration | | | | | | | | | | | |
| | 0 percent | | | 0.12 percent | | | 0.023 percent | | | 0.012 percent | | |
| | pH | Color (APHA) | TOC (ppm) | pH | Color (APHA) | TOC (ppm) | pH | Color (APHA) | TOC (ppm) | pH | Color (APHA) | TOC (ppm) |
| Initial | 3.37 | 13 | 15 | 3.38 | 15 | 17 | 4.51 | 9 | 7 | 5.01 | 3 | 4 |
| 24 hours | 3.17 | 200 | 117 | 3.48 | 90 | 42 | 3.17 | 143 | 60 | 3.1 | 180 | 83 |
| 48 hours | 3.01 | 383 | 221 | 3.40 | 110 | 48 | 3.30 | 198 | 77 | 2.91 | 286 | 129 |
| 72 hours | 2.84 | 592 | 349 | 3.35 | 122 | 56 | 3.00 | 227 | 89 | 2.82 | 385 | 190 |
| 96 hours | 2.78 | 861 | 511 | 3.35 | 138 | 61 | 2.90 | 255 | 101 | 2.60 | 523 | 265 |
| 120 hours | 2.69 | 1087 | 628 | 3.11 | 141 | 65 | — | — | — | 2.47 | 718 | 393 |
| 144 hours | 2.55 | 1439 | 849 | 3.09 | 155 | 70 | — | — | — | 2.38 | 925 | 541 |
| 168 hours | 2.28 | 1794 | 1113 | 3.07 | 162 | 74 | 2.59 | 292 | 121 | 2.32 | 1215 | 766 |

The results for Sample 9(C) from Table 2 show that the cation resin suffers substantial degradation due to the oxidation conditions of this test, and that the material that leaches into the water is acidic. Leaching of this material into bisphenol process streams would cause significant operational problems. The results for Samples 1, 2 and 3 from Table 2 show that the antioxidant suppresses the degradation of the cation resin, since only a minimal increase of the solution color and TOC is observed for these Samples. The solution pH is also shown to be stable after the initial equilibration of the water and the cation resin. The results of Table 2 also show that larger amounts of antioxidant are more effective in suppressing the oxidation of the cation resin.

Samples 5 and 7 from Part A of Example 1 were also tested as described above, and the results are shown in Table 3.

The results described in Table 3 above show that the antioxidant applied using solutions prepared with $H_2SO_4$ and $H_3PO_4$ in Part A of this Example 1 are just as effective in suppressing oxidation as the antioxidant applied using solutions prepared using HCl.

Part C: Washing the Aged Catalyst

In this Part C of Example 1, the aged cation resin of Samples 1 and 9(C) were washed to demonstrate that an antioxidant stabilized resin is more easily washed than an unstabilized resin in preparation for use in a bisphenol process.

The washing procedure was carried out as follows: 20 mL of a catalyst sample were placed in a graduated burette, with

TABLE 3

Results of Accelerated Aging Test
Effect of Acid Used in Antioxidant Treatment on Oxidation

| | SAMPLE NUMBER | | | | | | | | | | | |
|---|---|---|---|---|---|---|---|---|---|---|---|---|
| | 9 (C) | | | 1 | | | 5 | | | 7 | | |
| | Acid used to apply antioxidant | | | | | | | | | | | |
| | None | | | HCl | | | $H_2SO_4$ | | | $H_3PO_4$ | | |
| | Antioxidant Concentration | | | | | | | | | | | |
| | 0 percent | | | 0.12 percent | | | 0.12 percent | | | 0.12 percent | | |
| | pH | Color (APHA) | TOC (ppm) | pH | Color (APHA) | TOC (ppm) | pH | Color (APHA) | TOC (ppm) | pH | Color (APHA) | TOC (ppm) |
| Initial | 3.37 | 13 | 15 | 3.38 | 15 | 17 | 4.27 | 9 | 7 | 4.68 | 8 | 54 |
| 24 hours | 3.17 | 200 | 117 | 3.48 | 90 | 42 | 3.74 | 58 | 24 | 3.60 | 44 | 20 |
| 48 hours | 3.01 | 383 | 221 | 3.40 | 110 | 48 | — | — | — | — | — | — |
| 72 hours | 2.84 | 592 | 349 | 3.35 | 122 | 56 | — | — | — | — | — | — |
| 96 hours | 2.78 | 861 | 511 | 3.35 | 138 | 61 | 3.54 | 101 | 41 | 3.33 | 92 | 37 |
| 120 hours | 2.69 | 1087 | 628 | 3.11 | 141 | 65 | 3.50 | 109 | 54 | 3.25 | 105 | 46 |
| 144 hours | 2.55 | 1439 | 849 | 3.09 | 155 | 70 | 3.55 | 119 | 50 | 3.10 | 114 | 44 |
| 168 hours | 2.28 | 1794 | 1113 | 3.07 | 162 | 74 | — | — | — | — | — | — | glass wool at the bottom of the burette to retain the resin sample. Then, 40 mL of deionized water was added to the graduated burette and allowed to flow slowly through the resin. The wash water was collected, then tested for pH, TOC and color using the test methods described in Part A of this Example 1. Several washes of each sample were done using successive 40 mL aliquots of deionized water. The results are shown in Table 4.

TABLE 4

Results of Washing Aged Resin Samples

| | SAMPLE NUMBER | | | | | |
|---|---|---|---|---|---|---|
| | 9 (C) | | | 1 | | |
| | Resin Antioxidant Concentration | | | | | |
| Successive | 0 percent | | | 0.12 percent | | |
| Water Wash Aliquots | pH | Color (APHA) | TOC (ppm) | pH | Color (APHA) | TOC (ppm) |
| Before Washing | 2.06 | 1737 | 1355 | 3.00 | 164 | 97 |
| 1st | 3.43 | 71 | 59 | 3.92 | 15.6 | 21 |
| 2nd | 4.55 | 3.7 | 5.9 | 5.06 | 1.3 | 4.0 |
| 3rd | 4.96 | 2.2 | 2.8 | 5.47 | 2.0 | 2.4 |
| 4th | 4.78 | 2.6 | 2.7 | 5.07 | 1.3 | 1.8 |
| 5th | 4.86 | 2.1 | 3.0 | 5.30 | 1.5 | 1.9 |
| 6th | 5.04 | 2.6 | 2.5 | 5.38 | 1.1 | 1.7 |
| 7th | 5.10 | 1.8 | 2.3 | 5.46 | 1.8 | 1.6 |

The results described in Table 4 above demonstrate that low levels of wash water color and TOC are achieved more rapidly with the antioxidant-stabilized resin. The results of Table 4 also show that a high pH in the wash water is achieved more rapidly with the antioxidant-stabilized resin.

After washing the Samples with seven 40 mL aliquots of water, the water was drained from the aged catalyst samples, and the Samples were then washed with 40 mL aliquots of phenol using the above procedure. During the phenol washes the volume of each resin sample shrank from 20 mL to 13 mL. The color of the collected phenol aliquots was measured and the measurements are shown in Table 5. The first and fourth phenol aliquots were collected and allowed to age for 48 hours at 80° C. The phenol color was then remeasured, and is also shown in Table 5.

TABLE 5

Results of Phenol Wash of Aged and Washed Resin Samples

| | SAMPLE NUMBER | |
|---|---|---|
| | 9 (C) | 1 |
| Resin Antioxidant Concentration | 0 percent | 0.12 percent |
| Successive 40 mL Phenol Wash Aliquots | Color (APHA) | Color (APHA) |
| 1st | 22 | 18 |
| 2nd | 20 | 10 |
| 3rd | 18 | 11 |
| 4th | 15 | 8 |
| Phenol Wash Color After 48 Hours at 80° C. | | |
| 1st | 33 | 20 |
| 2nd | — | — |
| 3rd | — | — |
| 4th | 17 | 12 |

Even after the extensive water washing of the above Samples, some acidic leachables still remained in the resin and discolored the phenol. The acidic leachables caused a color increase in the phenol during storage at elevated temperature, and the color increase in the phenol used to wash the untreated resin was worse than for the treated resin. The tests conducted under this Part C of Example 1 demonstrate that the stabilized resin is easier to wash than the untreated resin. The results under this Part C of Example 1 also demonstrate that even extensive water washing is inadequate to remove all of the leachables from the untreated resin, and that the leachables can enter the phenol when it contacts the resin and cause degradation of the phenol.

EXAMPLE 2

Use of Stabilized Catalyst to Produce Bisphenol-A 1.2 grams (g) of 2,6-di-t-butyl-alpha-dimethylamino-p-cresol were dissolved in an acidified water solution. Then, the solution was slowly added to a stirred vessel containing 600 mL of DOWEX 50WX4 cation exchange resin and excess water. The above amount of 2,6-di-t-butyl-alpha-dimethylamino-p-cresol is enough to neutralize approximately 0.56 percent of the acid content of the cation exchange resin.

The treated cation exchange resin was rinsed thoroughly with deionized water, and then stored in a closed plastic container for three months.

After three months, the treated resin was removed from storage and found not to have discolored, as untreated cation resin usually does during this length of storage.

213 mL of the water-wet treated resin was placed in a flask with excess water. 8.47 g of dimethylthiazolidine (DMT) was slowly added to the flask while stirring. The excess water was removed from the treated resin, and then the treated resin was rinsed thoroughly with deionized water. A sample of this resin was tested by titration, and 22 percent of the acid sites of the resin were found to be neutralized.

15 mL of the DMT-promoted cation exchange resin was placed in a jacketed, continuous-flow reactor and dried by passing phenol over the resin. Phenol containing 4.05 percent acetone by weight was fed to the reactor, using a space-time velocity of 1 $hr^{-1}$ based on the water wet resin volume. The reactor temperature was maintained at 65° C. The product from the reactor was analyzed and found to contain 12.4 percent p,p'-bisphenol-A by weight. The selectivity was characterized by a 0.0298 ratio of o,p'-bisphenol-A to p,p'-bisphenol-A. The acetone conversion was found to be 75 percent.

What is claimed is:

1. A process for producing bisphenol A using a cation-exchange resin catalyst comprising:
    (a) providing a cation-exchange resin catalyst for catalyzing the condensation of phenol with acetone;
    (b) treating the cation-exchange resin catalyst with an antioxidant for preventing the degradation of the treated cation-exchange resin catalyst during storage, handling, processing and/or drying of the treated cation-exchange resin catalyst prior to using the treated cation-exchange resin catalyst in the process; and
    (c) condensing phenol and acetone in a reaction zone at a temperature range of from 20° C. to 200° C., in the presence of the treated cation-exchange resin catalyst.
2. The process of claim 1 including washing the treated cation-exchange resin catalyst with deionized water after the treatment step (b).

3. The process of claim 1 wherein the cation-exchange resin catalyst is a sulfonic acid-type cation-exchange resin catalyst.

4. The process of claim 3 wherein the cation-exchange resin catalyst is a sulfonated styrene-divinyl benzene copolymer.

5. The process of claim 1 wherein the antioxidant is a monocyclic or polycyclic phenol, an amine, a diamine, a thioester, a phosphate, a quinoline, or a mixture thereof.

6. The process of claim 1 wherein the antioxidant is 2,6-di-t-butyl-α-dimethylamino-p-cresol.

7. The process of claim 1 wherein the amount of antioxidant incorporated into the cation-exchange resin catalyst is from 0.001 to 10 percent by weight.

8. The process of claim 1 wherein the cation-exchange resin catalyst is stable when stored for three months or more.

9. The process of claim 1 wherein the color increase of water when contacted with the treated cation-exchange resin catalyst is less than 500 APHA during a seven day accelerated aging test.

10. The process of claim 1 wherein the increase in the TOC levels of water when contacted with the treated cation-exchange resin catalyst is less than 500 ppm during a seven day accelerated aging test.

11. The process of claim 1 further comprising preventing oxygen from contacting the catalyst so as to prevent the degradation of an ion-exchange resin catalyst during storage prior to using the treated catalyst in the process.

12. The process of claim 11 wherein oxygen is prevented from contacting the treated cation-exchange resin catalyst by storing the treated cation-exchange resin catalyst in the absence of oxygen by using oxygen barrier packaging, inert gas blanketing or vacuum packaging.

13. The process of claim 1 wherein the antioxidant treatment step (b) comprises dissolving the antioxidant in the water retained in the cation-exchange resin catalyst prior to use.

14. The process of claim 1 wherein the antioxidant treatment step (b) comprises partially neutralizing the acid functionality of the cation-exchange resin catalyst with the antioxidant.

15. The process of claim 1 wherein the antioxidant treatment step (b) of the cation-exchange resin catalyst comprises copolymerizing a monomer with antioxidant properties with other monomers to form the cation-exchange resin copolymer.

16. The process of claim 1 wherein the catalyst is treated with an antioxidant by polymerizing the antioxidant into a polymer resin.

\* \* \* \* \*